US00PP09915P

United States Patent [19]

Delbard

[11] Patent Number: Plant 9,915

[45] Date of Patent: Jun. 10, 1997

[54] HYBRID TEA ROSE PLANT NAMED 'DELEGO'

[75] Inventor: Guy Delbard, Hyeres, France

[73] Assignee: Societe Anonyme des Pepinieres et Roseraies Georges Delbard, Commentry, France

[21] Appl. No.: 643,040

[22] Filed: May 2, 1996

[51] Int. Cl.[6] ..... A01H 5/00

[52] U.S. Cl. ..... Plt./21

[58] Field of Search ..... Plt./20, 21

[56] References Cited

U.S. PATENT DOCUMENTS

P.P. 8,290 7/1993 Carmel ..... Plt./20

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided that abundantly forms attractive double flowers that are velvet red in coloration. Such flowers are long lasting and possess petals that detach cleanly. The plant exhibits an upright to bushy growth habit, forms semi-vigorous to vigorous vegetation, and is particularly well suited for greenhouse forcing for cut flower production. Additionally, the plant is very resistant to diseases when grown under greenhouse conditions and when grown outside in the garden.

1 Drawing Sheet

SUMMARY OF THE INVENTION

The new variety of Hybrid Tea Rose plant was created by artificial pollination wherein two parents were crossed which previously had been studied in the hope that they would contribute the desired characteristics. The female parent (i.e., the seed parent) was an unnamed seedling. The male parent (i.e., the pollen parent) resulted from the crossing of the 'Deladel' variety (U.S. Pat. No. P.P. 4,391) with the 'Korpek' variety (non-patented in the United States). The parentage of the new variety can be summarized as follows:

Unnamed Seedling×('Deladel'×'Korpek').

The seeds resulting from the above pollination were sown and 255 small plantlets were obtained which were physically and biologically different from each other. Selective study resulted in the identification of a single plant of the new variety.

It was found through careful study that the new variety of the present invention exhibits the following combination of characteristics:

(a) from a physical point of view it forms green mature wood, assumes an upright to bushy growth habit, and forms attractive long-lasting velvet red flowers having consistent petals which detach cleanly, and (b) from the biological point of view it forms semi-vigorous to vigorous vegetation, produces flowers in abundance, exhibits the ability readily to be forced, and is resistant to diseases when grown under greenhouse conditions and when grown outside.

The new variety well meets the needs of the horticultural industry and is particularly well suited for growing in the greenhouse for the production of attractive long-lasting velvet red cut flowers.

The new variety can be readily distinguished from other varieties in view of the combination of characteristics described herein. It exhibits long and relatively straight stems, rigid and substantially straight peduncles, an excellent ability to be forced under greenhouse conditions, and a long vase life for its distinctive velvet red blossoms.

The new variety has been found to undergo asexual propagation and can be readily reproduced by conventional routes, such as budding (i.e., eye grafting). This asexual reproduction by budding as performed in France has demonstrated that the characteristics of the new variety are strictly transmissible from one generation to another and are firmly fixed.

The new variety has been named the 'Delego' variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in the South of France.

1 — illustrates a specimen of a young shoot;

2 — illustrates a specimen of a floral bud at the opening of the sepals;

3 — illustrates a specimen of a floral bud at the opening of the petals;

4 — illustrates a specimen of a flower in the course of opening;

5 — illustrates a specimen of an open flower in a more advanced stage of opening;

6 — illustrates a specimen of an open flower — plan view — obverse;

7 — illustrates a specimen of a fully open flower — plan view — obverse;

8 — illustrates a specimen of a fully open flower — plan view — reverse;

9 — illustrates a specimen of an open flower — plan view — reverse;

10 — illustrates a specimen of a floral receptacle showing the arrangement of the stamens and pistils;

11 — illustrates a specimen of a floral receptacle showing the arrangement of the pistils (sepals and stamens removed);

12 — illustrates a specimen of a flowering stem;

13 — illustrates a specimen of a main branch;

14 — illustrates a specimen of a leaf with three leaflets — plan view — upper surface;

15 — illustrates a specimen of a leaf with five leaflets — plan view — upper surface;

16 — illustrates a specimen of a leaf with three leaflets — plan view — under surface; and

17 — illustrates a specimen of a leaf with five leaflets — plan view — under surface.

DETAILED DESCRIPTION

The chart used in the identification of the colors is that of The Royal Horticultural Society (R.H.S. Colour Chart). The description is based on the observation of plants grown under glass in the South of France. The coloration in common terms sometimes also is provided.

Class: Hybrid Tea.

Plant:

*Height.*—Plants which were pruned to a height of 1 m. produce floral stems having a length of approximately 40 to 100 cm., and an average length of approximately 70 cm.

*Habit.*—Upright to bushy.

Branches:

*Color.*—Young shoots: when approximately 20 cm. long, exhibit a green coloration, Yellow-Green Group 146C. Floral stems: Yellow-Green Group 146B. Mature wood: Yellow-Green Group 146A to 146B.

*Thorns.*—Configuration: concave on the upper and under edges. Quantity and frequency: on a typical stem having a length of 70 cm., no thorns commonly appear on the first 30 cm. under the bud; on the next 20 cm. of the stem, thorns of approximately 5 to 7 mm. in length commonly appear while separated at approximately 1.5 cm.; and on the final 20 cm. of the stem many thorns of approximately 1 mm. in length and thorns of approximately 7 mm. in length are irregularly presented. Length: approximately 5 mm. on average on floral stems and approximately 7 mm. on average on mature wood, and commonly range in length from approximately 1 to 8 mm. in each instance. Color: on young shoots of approximately 3 cm. in length there commonly are no thorns; on floral stems the coloration of the thorns is Yellow-Green Group 146D, and on mature wood the coloration of the thorns is Greyed-Orange Group 165A to 165B (havana brown).

*Leaves.*—Number: typical for the class. Size: Medium. Stipules: adnate, medium and typical for the class.

*Leaflets.*—Number: commonly 3, 5 (most common, and 7 . Size: medium. Shape: obtuse to rounded at the base of terminal leaflet; and convex in cross-section. Serration: present, single but not necessarily regular. The serration is not regular in the sense that each ridge is necessarily of the same size. General appearance: consistent, and medium in glossiness. Petiole: the inner surface is grooved with non-glandular edges. Petiole color on young shoot: green with bronze coloration, Greyed-Orange Group 173A, with the green coloration being more prominent at the base. Petiole color on floral stem: Yellow-Green Group 146A on upper surface and Yellow-Green Group 146C on under surface. Petiole color on mature wood: Yellow-Green Group 146A on upper surface and Yellow-Green Group 146C on under surface. Petiole length of terminal leaflet: approximately 19 to 31 mm., approximately 21 mm. on average, with a standard deviation of 0.2 mm. Terminal leaflet length: approximatey 60 to 90 mm., approximately 72 mm. on average, with a standard deviation of 0.5 mm. Terminal leaflet width: approximately 40 to 63 mm., approximately 47 mm. on average, with a standard deviation of 0.3 mm. Terminal leaflet shape at base: obtuse to rounded. Leaflet color of young shoot: Yellow-Green Group 147A with bronze coloration on the upper surface and Greyed-Purple Group 183C with green coloration towards the center of the leaflet on the under surface. Leaflet color on floral stem: Green Group 137A on the upper surface and Yellow-Green Group 147B on the under surface. Leaflet color of mature wood: Green Group 137A to 137B on the upper surface, and Yellow-Green Group 147B to 147C on the under surface.

Inflorescence:

*Number of flowers.*—Generally one per stem when grown under forced greenhouse conditions; however, sometimes in such forced culture the first axillary eyes below the flower develop and form approximately 3 to 5 flowers.

*Peduncle.*—Erect, stiff, Yellow-Green Group 146B in coloration with some small hairs, and commonly approximately 70 to 112 mm. in length (approximately 95 mm. in length on average).

*Sepals.*—Configuration: commonly the sepals are approximately 45 mm. in length on average. Commonly approximately 3 of the sepals will possess medium to long extensions, and approximately 2 of the sepals will be devoid of extensions. Color: Green Group 138B on the upper surface, and Yellow-Green Group 144A on the under surface.

*Buds.*—Shape: ovate in longitudinal section immediately prior to the opening of the sepals. Size before calyx breaks: the bud lengths are approximately 30 to 35 mm., with an average length of approximately 32 mm. Size after calyx breaks: the bud lengths are approximately 53 to 60 mm, with an average length of approximately 55 mm. Color: as the calyx breaks and the petals open, the color is near Red Group 46A but darker.

*Flower.*—Time: early flowering. Shape: double. Form: irregularly rounded when viewed from above, flattened convex at the upper part when viewed from the side, and flattened convex to convex at the lower part when viewed from the side. Diameter: medium to large, approximately 9.7 to 11.3 cm., and approximately 10.7 cm. on average, with a standard deviation of 0.5 cm. Petal number: commonly approximately 27 to 42, and an average of approximately 36. Petal size (second row from outside): the length is approximately 51 to 57 mm. with a mean of approximately 57 mm., and a standard deviation of 0.2 mm.; and the width is approximately 55 to 67 mm. with a mean of approximately 62 mm., and a standard deviation of 0.5 mm. Petal shape: the first row of petals commonly exhibit a broad ovate configuration, the undulation of the petal margin is average, and the reflexing of the margin is average when the flower is open. Petal color: The following description of a nearly fully open flower was made during April while observing a flower that had been undergoing opening for 3 days. Petal color (middle zone): on the inner surface red velvet, Red Group 53A, and on the outer surface red velvet, Red Group 46A. Petal color (marginal zone): on the inner surface red-velvet, Red Group 53A, on the outer surface red velvet, Red Group 46A. Petal spot at base: very small and sometimes no spot is apparent when grown outside. Color of spot inner side: Yellow Group 7A. Color of spot outer side: pale yellow, Yellow Group 4C and 4D. Stamens: approximately 105 in number and are somewhat regularly arranged around and generally below the maximum height of the pistils. Filaments: not all possess an anther, medium in length and Yellow Group 4C in coloration. Anthers: medium in size, each opens at approximately the same time, and the immature coloration is Yellow Group 13B. Pollen: the quantity of the pollen grains is few and they commonly are Yellow-Orange Group 15A in coloration. Pistils: approximtely 80 in number. Styles: medium in length and Red-Purple 66C in coloration. Stigmas: Yellow Group 4C, and generally are present at approximately the same level as the anthers, but a few anthers may be higher. Hips: in longitudinal section they are in the shape of a funnel, and they are approximately 23 mm. in diameter. Seeds: small to medium in size, commonly approximately 10 to 15 in number, and average approximately 12 in number. Petal drop: petals detach cleanly. Fragrance: none. Lasting quality: long. When cut and placed in a vase, the flowers commonly last approximately 10 days. The lasting quality of the flowers varies depending upon temperature and the season of the year.

Development:

*Vegetation.*—Semi-vigorous to vigorous.

*Blooming.*—Very abundant and almost continuous.

*Aptitude to forcing.*—Excellent.

*Resistance to diseases.*—Very good under greenhouse conditions, and also when grown outside.

I claim:

1. A new and distinct variety of Hybrid Tea rose plant characterized by the following combination of characteristics:

(a) from a physical point of view it forms green mature wood, assumes an upright to bushy growth habit, and forms attractive long-lasting velvet red flowers having consistent petals which detach cleanly, and (b) from the biological point of view forms semi-vigorous to vigorous vegetation, produces flowers in abundance, exhibits the ability readily to be forced, and is very resistant to diseases when grown under greenhouse conditions and when grown outside;

substantially as herein shown and described.

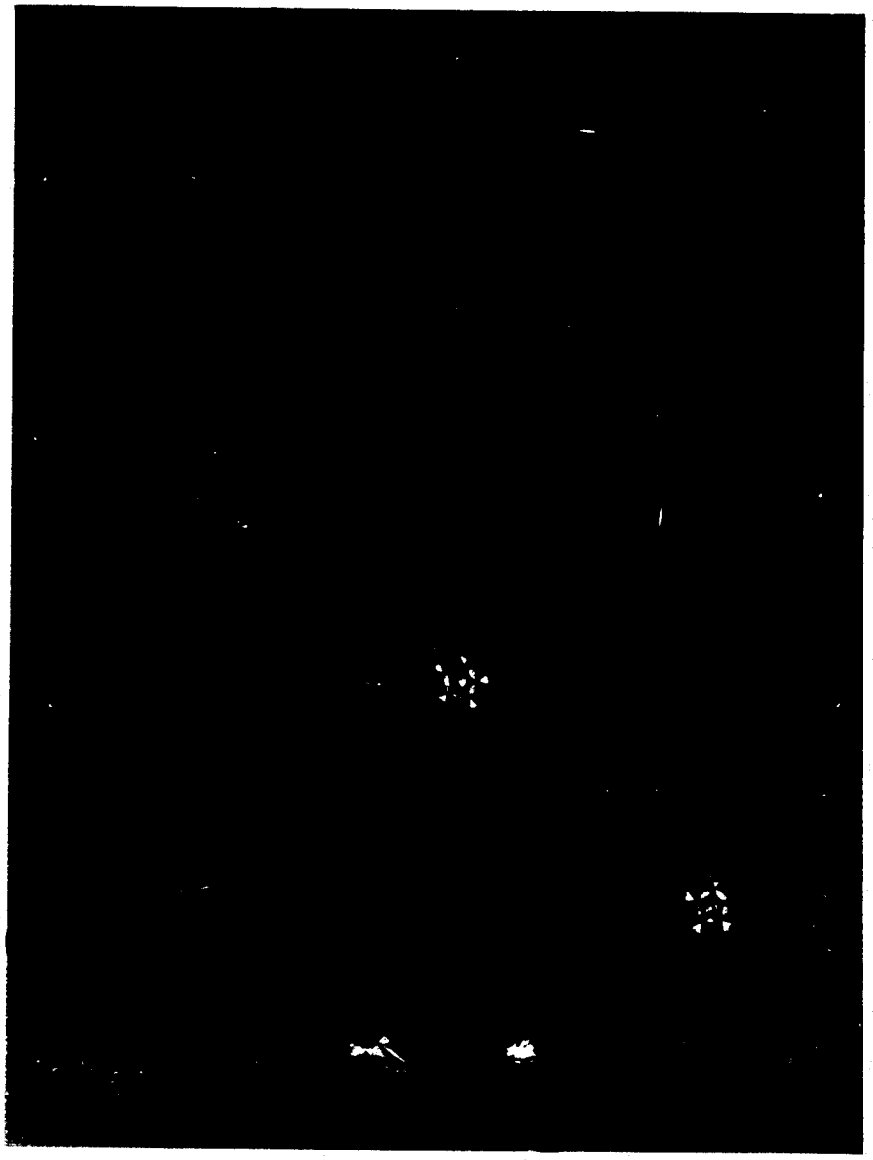

* * * * *